(12) United States Patent
Fuchigami et al.

(10) Patent No.: US 11,139,067 B2
(45) Date of Patent: Oct. 5, 2021

(54) MEDICAL IMAGE DISPLAY DEVICE, METHOD, AND PROGRAM

(71) Applicant: FUJIFILM Corporation, Tokyo (JP)

(72) Inventors: Takuya Fuchigami, Tokyo (JP); Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 95 days.

(21) Appl. No.: 16/235,154

(22) Filed: Dec. 28, 2018

(65) Prior Publication Data

US 2019/0267132 A1 Aug. 29, 2019

(30) Foreign Application Priority Data

Feb. 28, 2018 (JP) .............................. JP2018-035200

(51) Int. Cl.
| | |
|---|---|
| *G16H 30/40* | (2018.01) |
| *G16H 50/20* | (2018.01) |
| *G06T 11/60* | (2006.01) |
| *G16H 15/00* | (2018.01) |
| *G06F 17/00* | (2019.01) |

(52) U.S. Cl.
CPC ............. *G16H 30/40* (2018.01); *G06T 11/60* (2013.01); *G16H 50/20* (2018.01); *G06T 2210/41* (2013.01); *G16H 15/00* (2018.01)

(58) Field of Classification Search
CPC ........ G16H 30/40; G16H 50/20; G16H 15/00; G06T 11/60; G06T 2210/41
See application file for complete search history.

(56) References Cited

U.S. PATENT DOCUMENTS

| | | | | |
|---|---|---|---|---|
| 9,589,374 | B1* | 3/2017 | Gao ...................... | G06T 11/008 |
| 2005/0107690 | A1* | 5/2005 | Soejima ................ | G16H 15/00 |
| | | | | 600/425 |
| 2005/0226405 | A1 | 10/2005 | Fukatsu et al. | |
| 2006/0269111 | A1* | 11/2006 | Stoecker ............... | G16H 50/20 |
| | | | | 382/128 |
| 2010/0053213 | A1* | 3/2010 | Ishida .................... | G16H 30/40 |
| | | | | 345/629 |

(Continued)

FOREIGN PATENT DOCUMENTS

| | | |
|---|---|---|
| JP | 2005-301453 A | 10/2005 |
| JP | 2007-287027 A | 11/2007 |

(Continued)

OTHER PUBLICATIONS

Japanese Office Action, dated Dec. 22, 2020, for Japanese Application No. 2018-035200, with an English translation.

*Primary Examiner* — Quoc A Tran
(74) *Attorney, Agent, or Firm* — Birch, Stewart, Kolasch & Birch, LLP

(57) ABSTRACT

An analysis unit analyzes a medical image and acquires an analysis result. An interpretation report creation unit creates an interpretation report on a disease based on the analysis result. A display control unit displays the medical image and the interpretation report on a display. In response to an instruction to modify one of a disease region in the medical image and a description of the disease region in the interpretation report, a modification unit modifies the other one of the disease region in the medical image and the description of the disease region in the interpretation report.

13 Claims, 10 Drawing Sheets

(56) References Cited

U.S. PATENT DOCUMENTS

| | | | | |
|---|---|---|---|---|
| 2016/0203263 | A1* | 7/2016 | Maier | G06T 7/0016 |
| | | | | 705/2 |
| 2018/0144828 | A1* | 5/2018 | Baker | G16H 50/70 |
| 2019/0122363 | A1* | 4/2019 | Greveson | A61B 6/501 |
| 2021/0018742 | A1* | 1/2021 | Stumpe | G06K 9/00147 |

FOREIGN PATENT DOCUMENTS

| | | | |
|---|---|---|---|
| JP | 2008-108079 | A | 5/2008 |
| JP | 2009-238038 | A | 10/2009 |
| JP | 2015-950403 | A | 5/2015 |
| JP | 2017-33257 | A | 2/2017 |
| JP | 2017-68801 | A | 4/2017 |

\* cited by examiner

MEDICAL IMAGE DISPLAY DEVICE, METHOD, AND PROGRAM

CROSS REFERENCE TO RELATED APPLICATIONS

The present application claims priority under 35 U.S.C. § 119 to Japanese Patent Application No. 2018-035200 filed on Feb. 28, 2018. The above application is hereby expressly incorporated by reference, in its entirety, into the present application.

BACKGROUND

Field of the Invention

The present invention relates to a medical image display device, method, and program for displaying a medical image and an interpretation report.

Related Art

In recent years, advances in medical apparatuses, such as computed tomography (CT) apparatuses and magnetic resonance imaging (MRI) apparatuses, have enabled image diagnosis using high-resolution medical images with higher quality. In particular, in a case where a target part is a brain, a region causing a vascular disorder, such as cerebral infarction and cerebral hemorrhage, can be specified by image diagnosis using CT images, MRI images, and the like. Therefore, appropriate treatment based on the specified result is performed.

A medical image is analyzed by computer-aided diagnosis (CAD) using a discriminator learned by deep learning or the like, a disease region such as a bleeding region and an infarction region in the brain and an ischemic region in the heart, the volume of a disease region, and the like are extracted, and these are acquired as the analysis result. The analysis result generated by analysis processing in this manner is stored in a database so as to be associated with examination information, such as a patient name, gender, age, and a modality that has acquired the medical image, and provided for diagnosis. At this time, a technician in a radiology department or the like, who has acquired the medical image, determines a radiologist according to the medical image, and notifies the determined radiologist that the medical image and the result of analysis by the CAD are present. The radiologist interprets the medical image with reference to the transmitted medical image and analysis result and creates an interpretation report at his or her own interpretation terminal.

Various methods for supporting interpretation of medical images by such a radiologist have been proposed. For example, JP2009-238038A has proposed a method of displaying an annotation corresponding to the position of a lesion described in an interpretation report on a medical image in the case of displaying the medical image and the interpretation report side by side. In the method described in JP2009-238038A, in a case where the interpretation report to be displayed is changed, the medical image is also changed, and the position of the annotation displayed on the medical image is changed according to the content of the changed interpretation report. JP2017-068801A has proposed a method of displaying a medical image display screen including a medical image and comments in a case where a diagnosis result described in the interpretation report is modified.

On the other hand, in a case where the result of the analysis by CAD is incorrect, the radiologist needs to modify the position of a region of a disease (hereinafter, referred to as a disease region) shown in the medical image. In accordance with the modification of the position of the disease region in the medical image, it is also necessary to rewrite a description of the disease of the interpretation report. However, the operation of modifying both the medical image and the interpretation report is burdensome to the radiologist.

SUMMARY

The invention has been made in view of the above circumstances, and it is an object of the invention to reduce the burden on the operator, such as a radiologist, in the case of performing an operation of modifying both a medical image and an interpretation report.

A medical image display device according to the invention comprises: a display control unit that displays a medical image including a disease and an interpretation report including a description of the disease on a display unit; and a modification unit that modifies, in response to an instruction to modify one of a region of the disease in the medical image and the description of the disease in the interpretation report, the other one of the region of the disease in the medical image and the description of the disease in the interpretation report.

In the medical image display device according to the invention, the interpretation report may include a certainty factor that the region of the disease in the medical image is a disease.

In the medical image display device according to the invention, the medical image may be a brain image, and the disease may be cerebral infarction.

In the medical image display device according to the invention, the interpretation report may be associated with a past interpretation report of the same patient.

In the medical image display device according to the invention, the interpretation report may be associated with a past medical image of the same patient associated with the past interpretation report.

In the medical image display device according to the invention, the interpretation report may include ASPECTS.

"ASPECTS" is an abbreviation for Alberta Stroke Program Early CT Score, and is a scoring method for quantifying the early CT sign of simple CT for cerebral infarction in the middle cerebral artery region. Specifically, in a case where the medical image is a CT image, the ASPECTS is a method in which the middle cerebral artery region is classified into ten regions in two representative cross sections (basal ganglia level and radiological crown level), the presence or absence of early ischemic change is evaluated for each region, and the positive part is scored by a penalty point method. In a case where the medical image is an MRI image, in particular, a diffusion weighted image, the middle cerebral artery region is classified into eleven regions in two representative cross sections (basal ganglia level and radiological crown level) and scoring is performed. In ASPECTS, the lower the score, the wider the area of the infarction region. ASPECTS may be used to determine whether to apply tPA intravenous therapy, which is one of methods for treating cerebral infarction.

The medical image display device according to the invention may further comprise an analysis unit that analyzes the medical image and acquires an analysis result on the disease.

In this case, the medical image display device according to the invention may further comprise an interpretation report creation unit that creates the interpretation report based on the analysis result.

A medical image display method according to the invention comprises: displaying a medical image including a disease and an interpretation report including a description of the disease on a display unit; and modifying, in response to an instruction to modify one of a region of the disease in the medical image and the description of the disease in the interpretation report, the other one of the region of the disease in the medical image and the description of the disease in the interpretation report.

In addition, a program causing a computer to execute the medical image display method according to the invention may be provided.

Another medical image display device according to the invention comprises: a memory that stores commands to be executed by a computer; and a processor configured to execute the stored commands. The processor executes: a step of displaying a medical image including a disease and an interpretation report including a description of the disease on a display unit; and a step of modifying, in response to an instruction to modify one of a region of the disease in the medical image and the description of the disease in the interpretation report, the other one of the region of the disease in the medical image and the description of the disease in the interpretation report.

According to the invention, a medical image including a disease and an interpretation report including a description of the disease are displayed on the display unit, and the other one of the region of the disease in the medical image and the description of the disease in the interpretation report is modified in response to an instruction to modify one of the region of the disease in the medical image and the description of the disease in the interpretation report. For this reason, even in a case where it is necessary to modify both the medical image and the interpretation report, the other one is modified according to the modification of one of the medical image and the interpretation report. Therefore, it is possible to reduce the burden on the operator who modifies the medical image and the interpretation report.

DETAILED DESCRIPTION

Figure 1:
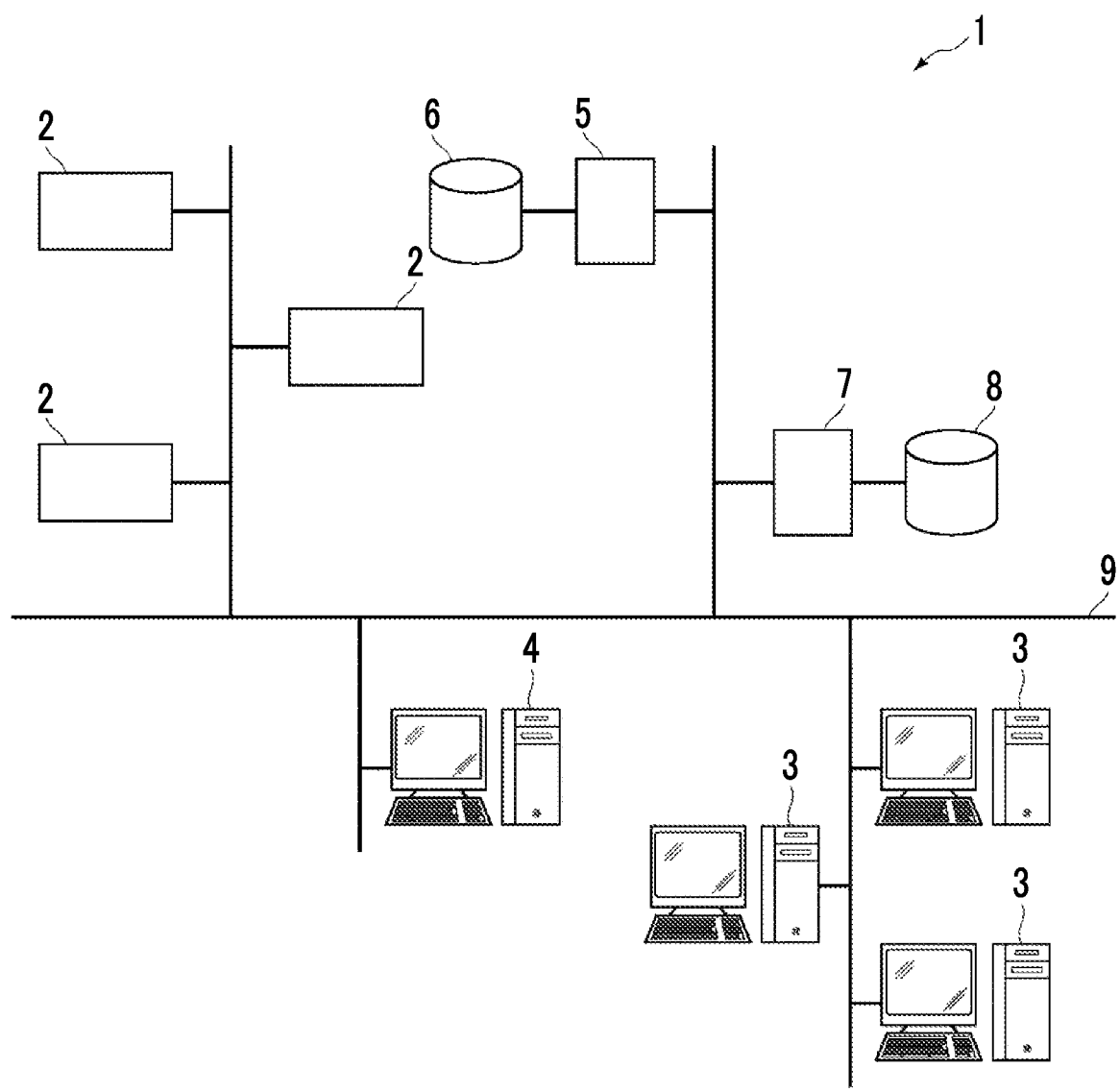
FIG. 1 is a diagram showing the schematic configuration of a medical information system to which a medical image display device according to a first embodiment of the invention is applied.

Hereinafter, an embodiment of the invention will be described with reference to the accompanying diagrams. FIG. 1 is a diagram showing the schematic configuration of a medical information system to which a medical image display device according to an embodiment of the invention is applied. A medical information system 1 shown in FIG. 1 is a system for performing imaging of an examination target part of a subject, storage of a medical image acquired by imaging, interpretation of a medical image by a radiologist and creation of an interpretation report, and viewing of an interpretation report by a doctor in a medical department of a request source and detailed observation of a medical image to be interpreted, based on an examination order from a doctor in a medical department using a known ordering system. As shown in FIG. 1, the medical information system 1 is configured to include a plurality of modalities (imaging apparatuses) 2, a plurality of interpretation workstations (WS) 3 that are interpretation terminals, a medical department workstation (WS) 4, an image server 5, an image database 6, an interpretation report server 7, and an interpretation report database 8 that are communicably connected to each other through a wired or wireless network 9. The medical image display device of the present embodiment is applied to the interpretation WS 3.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed onto the computer from the recording medium. Alternatively, the application program is stored in a storage device of a server computer connected to the network 9 or in a network storage so as to be accessible from the outside, and is downloaded and installed onto the computer as necessary.

The modality 2 is an apparatus that generates a medical image showing a diagnosis target part by imaging the diagnosis target part of the subject. Specifically, the modality 2 is a simple X-rays imaging apparatus, a CT apparatus, an MRI apparatus, a positron emission tomography (PET) apparatus, and the like. A medical image generated by the modality 2 is transmitted to the image server 5 and stored therein.

The interpretation WS 3 includes the medical image display device according to the present embodiment. The configuration of the interpretation WS 3 will be described later.

The medical department WS 4 is a computer used by a doctor in a medical department to observe the details of an image, view an interpretation report, create an electronic medical record, and the like, and is configured to include a processing device, a high-definition display, and an input device such as a keyboard and a mouse. In the medical department WS 4, each process, such as sending a request to view an image to the image server 5, display of an image received from the image server 5, automatic detection or highlighting of a lesion-like portion in an image, sending a request to view an interpretation report to the interpretation report server 7, and display of an interpretation report received from the interpretation report server 7, is performed by executing a software program for each process.

The image server 5 is obtained by installing a software program for providing a function of a database management system (DBMS) on a general-purpose computer with a relatively high processing capacity. The image server 5 comprises a large-capacity storage for an image database 6. This storage may be a large-capacity hard disk device connected to the image server 5 by a data bus, or may be a disk device connected to a storage area network (SAN) or a network attached storage (NAS) connected to the network 9. In a case where the image server 5 receives a request to register a medical image from the modality 2, the image server 5 registers the medical image in the image database 6 in a format for a database.

Image data and accessory information of medical images acquired by the modality 2 are registered in the image database 6. The accessory information includes, for example, an image ID for identifying each medical image, a patient identification (ID) for identifying a subject, an examination ID for identifying an examination, a unique ID (UID: unique identification) allocated for each medical image, examination date and examination time at which the medical image is generated, the type of a modality used in an examination for acquiring a medical image, patient information such as patient's name, age, and gender, an examination part (imaging part), imaging information (an imaging protocol, an imaging sequence, an imaging method, imaging conditions, the use of a contrast medium, and the like), and information such as a series number or a collection number in a case where a plurality of medical images are acquired in one examination.

In a case where a viewing request from the interpretation WS 3 is received through the network 9, the image server 5 searches for a medical image registered in the image database 6 and transmits the searched medical image to the interpretation WS 3 that is a request source.

The interpretation report server 7 has a software program for providing a function of a database management system to a general-purpose computer. In a case where the interpretation report server 7 receives a request to register an interpretation report from the interpretation WS 3, the interpretation report server 7 registers the interpretation report in the interpretation report database 8 in a format for a database. In a case where a request to search for an interpretation report is received, the interpretation report is searched for from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, findings, and the certainty factor of findings, is recorded.

The network 9 is a wired or wireless local area network that connects various apparatuses in a hospital to each other. In a case where the interpretation WS 3 is installed in another hospital or clinic, the network 9 may be configured to connect local area networks of respective hospitals through the Internet or a dedicated circuit. In any case, it is preferable that the network 9 is configured to be able to realize high-speed transmission of medical images, such as an optical network.

Hereinafter, the interpretation WS 3 according to the present embodiment will be described in detail. The interpretation WS 3 is a computer used by a radiologist of a medical image to interpret the medical image and create the interpretation report, and is configured to include a processing device, a high-definition display, and an input device such as a keyboard and a mouse. In the interpretation WS 3, each process, such as making a request to view a medical image to the image server 5, various kinds of image processing on a medical image received from image server 5, display of a medical image, analysis processing on a medical image, highlighting of a medical image based on the analysis result, creation of an interpretation report based on the analysis result, support for the creation of an interpretation report, making a request to register an interpretation report and a request to view an interpretation report to the interpretation report server 7, and display of an interpretation report received from the interpretation report server 7, is performed by executing a software program for each process. Since processes other than the process performed by the medical image display device of the present embodiment, among these processes, are performed by a known software program, the detailed description thereof will be omitted herein. The processes other than the process performed by the medical image display device of the present embodiment may not be performed in the interpretation WS 3, and a computer that performs the processes may be separately connected to the network 9, and requested processing on the computer may be performed according to a processing request from the interpretation WS 3.

The interpretation WS 3 includes the medical image display device according to the present embodiment. Therefore, a medical image display program according to the present embodiment is installed on the interpretation WS 3. The medical image display program is recorded on a recording medium, such as a DVD or a CD-ROM, and distributed, and is installed onto the interpretation WS 3 from the recording medium. Alternatively, the medical image display program is stored in a storage device of a server computer connected to the network or in a network storage so as to be accessible from the outside, and is downloaded and installed onto the interpretation WS 3 as necessary.

Figure 2:
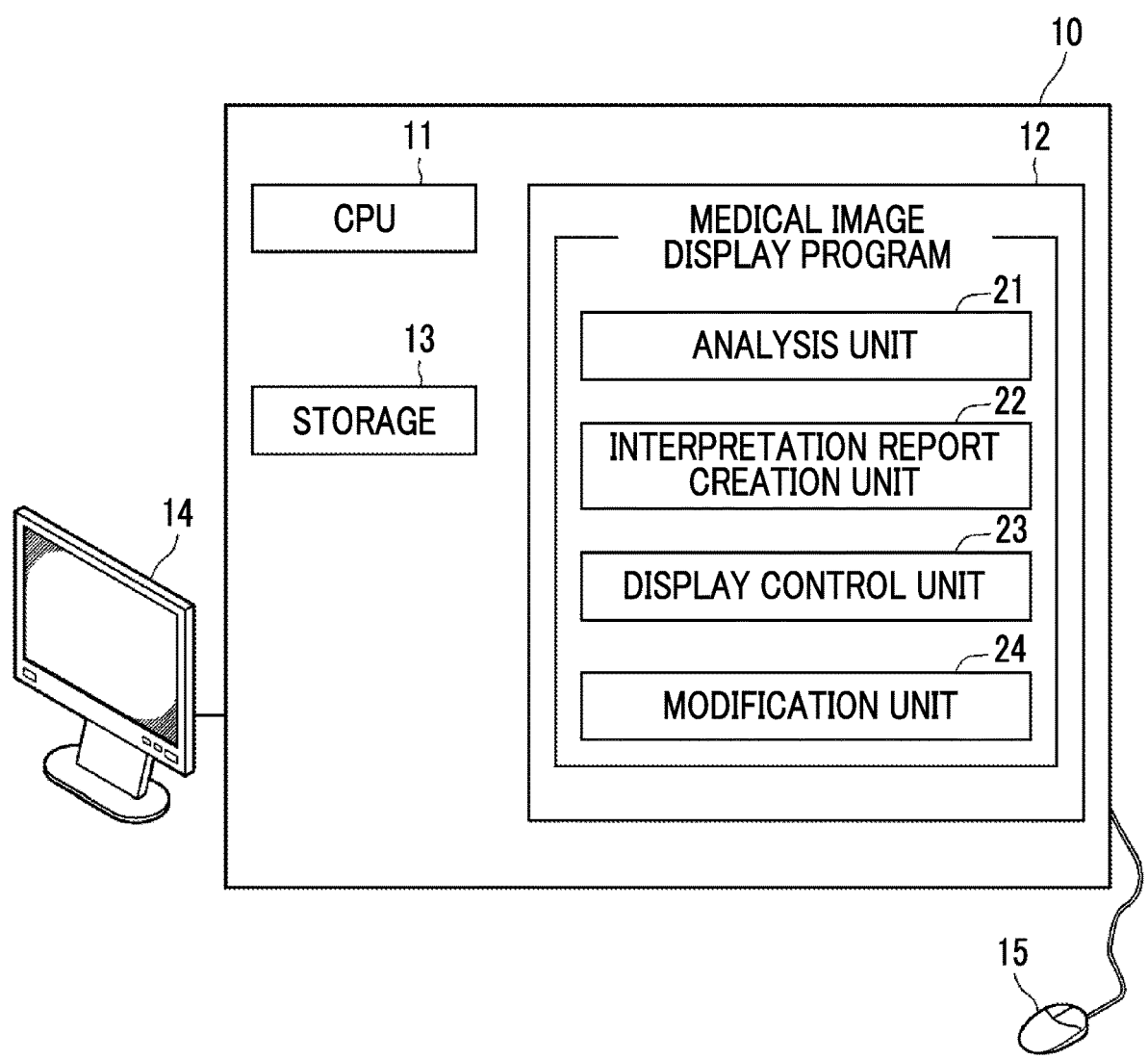
FIG. 2 is a diagram showing the schematic configuration of the medical image display device according to the first embodiment of the invention.

FIG. 2 is a diagram showing the schematic configuration of a medical image display device according to a first embodiment of the invention that is realized by installing the medical image display program. As shown in FIG. 2, a medical image display device 10 comprises a central processing unit (CPU) 11, a memory 12, and a storage 13 as the configuration of a standard computer. A display 14, such as a high-definition liquid crystal display, and an input device (hereinafter, referred to as an input unit) 15, such as a keyboard and a mouse, are connected to the medical image display device 10. The display 14 corresponds to a display unit.

The storage 13 is a storage device, such as a hard disk or a solid state drive (SSD). Medical images and various kinds of information including information necessary for processing of the medical image display device 10, which are acquired from the image server 5 through the network 9, are stored in the storage 13.

A medical image display program is stored in the memory 12. As processing to be executed by the CPU 11, the medical image display program defines: analysis processing for analyzing a medical image including a disease and generating an analysis result on the disease; interpretation report generation processing for generating an interpretation report including a description of the disease based on the analysis result; display control processing for displaying the medical image and the interpretation report on the display 14; and modification processing for modifying, in response to an instruction to modify one of the disease region in the medical image and the description of the disease in the interpretation report, the other one of the disease region in the medical image and the description of the disease in the interpretation report.

The CPU 11 executes these processes according to the medical image display program, so that the computer functions as an analysis unit 21, an interpretation report creation unit 22, a display control unit 23, and a modification unit 24. In the present embodiment, the CPU 11 executes the function of each unit according to the medical image display program. However, as a general-purpose processor that executes software to function as various processing units, a programmable logic device (PLD) that is a processor whose circuit configuration can be changed after manufacturing, such as a field programmable gate array (FPGA), can be used in addition to the CPU 11. Alternatively, the processing of each unit may also be executed by a dedicated electric circuit that is a processor having a circuit configuration designed exclusively to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA).

Alternatively, a plurality of processing units may be configured by one processor. As an example of configuring a plurality of processing units using one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

The analysis unit 21 analyzes a medical image and acquires an analysis result on a disease included in the medical image. For this reason, the analysis unit 21 performs analysis processing for extracting a disease region in the medical image. In the present embodiment, it is assumed that the medical image is an MRI image of the brain. However, the medical image may be a CT image. In the present embodiment, the analysis unit 21 determines the anatomical position and size of an infarction region in the brain, the type of infarction (hyperacute or old?), and the certainty factor of the type of infarction. The analysis unit 21 generates character information to be described in the interpretation report based on the analysis result of the medical image. For example, in a case where an infarction region 30 of 10 $cm^3$ in the hyperacute phase is extracted with a reliability of 0.9 at a part a in the brain, "part a", "10 $cm^3$", "hyperacute infarction", and "reliability 0.9" are generated as character information. In a case where an old infarction region of 5 $cm^3$ is extracted with a reliability of 0.6 at a part b in the brain, "part b", "5 $cm^3$", "old infarction", and "reliability 0.6" are generated as character information. In the present embodiment, it is assumed that the analysis unit 21 acquires the anatomical position and size of an infarction region in the brain, the type of infarction (hyperacute or old?), the certainty factor of the type of infarction, and such character information as an analysis result.

The analysis unit 21 comprises a discriminator that is machine-learned to determine whether or not each pixel (voxel) in a medical image is an infarction region and the type of the infarction region. In the present embodiment, the discriminator is a neural network deep-learned so as to be able to classify a plurality of types of lesion regions included in a medical image. The discriminator is learned so as to output a probability that each pixel (voxel) in a medical image is a hyperacute infarction and a probability that each pixel (voxel) in a medical image is an old infarction in a case where the medical image is input. Then, in a case where the probability output for a certain pixel is equal to or greater than a predetermined threshold value, the discriminator determines that the pixel is an infarction of a type having a probability equal to or greater than the threshold value.

For a certain type of infarction, the analysis unit 21 calculates a statistical value (for example, an average value, a mode, or a maximum value) of the probability output by the discriminator for all pixels within a region, in which the probability output by the discriminator is equal to or greater than the threshold value, as the certainty factor of the certain type of infarction in the region. In addition, the analysis unit 21 calculates the size of the infarction region by multiplying the number of pixels included in a region, which is configured to include pixels determined to be a region of a certain type of infarction (hereinafter, simply referred to as an infarction region), by the volume per pixel in the medical image. The unit of the size of the infarction region is assumed to be cubic centimeter.

The interpretation report creation unit 22 creates an interpretation report on the disease based on the analysis result of the analysis unit 21. The interpretation report creation unit 22 performs machine learning so as to make the character information generated by the analysis unit 21 into sentences. Therefore, in a case where the character information generated by the analysis unit 21 is input, the interpretation report creation unit 22 creates sentences of the interpretation report on the medical image. For example, in a case where "part a", "10 $cm^3$", "hyperacute infarction", and "reliability 0.9" are input as character information, a sentence "there is an infarction in the hyperacute phase at the part a, size=10 $cm^3$, certainty factor=0.9" is created. In a case where "part b", "5 $cm^3$", "old infarction", and "reliability 0.6" are input as character information, a sentence "there is an old infarction at the part b, size=5 $cm^3$, certainty factor=0.6". In the present embodiment, the interpretation report creation unit 22 is configured to include a neural network deep-learned so as to create an interpretation report from the character information.

In a case where "old infarction" is input as character information, the interpretation report creation unit 22 instructs the interpretation report server 7 to search for a past interpretation report on the patient whose medical image, for which an interpretation report is being created, has been acquired. The interpretation report server 7 searches for the interpretation report database 8 based on the instruction. In a case where the past interpretation report is found, the interpretation report server 7 transmits link information indicating the storage location of the past interpretation report to the interpretation WS 3. The past interpretation report includes a link to a past medical image referred to at the time of creating the interpretation report. The interpretation report creation unit 22 sets the link transmitted from the interpretation report server 7 for a sentence including the character information of "old infarction" out of the created sentences.

The discriminator and the interpretation report creation unit 22 can use a support vector machine (SVM) and the like in addition to the deep learned neural network.

Figure 3:
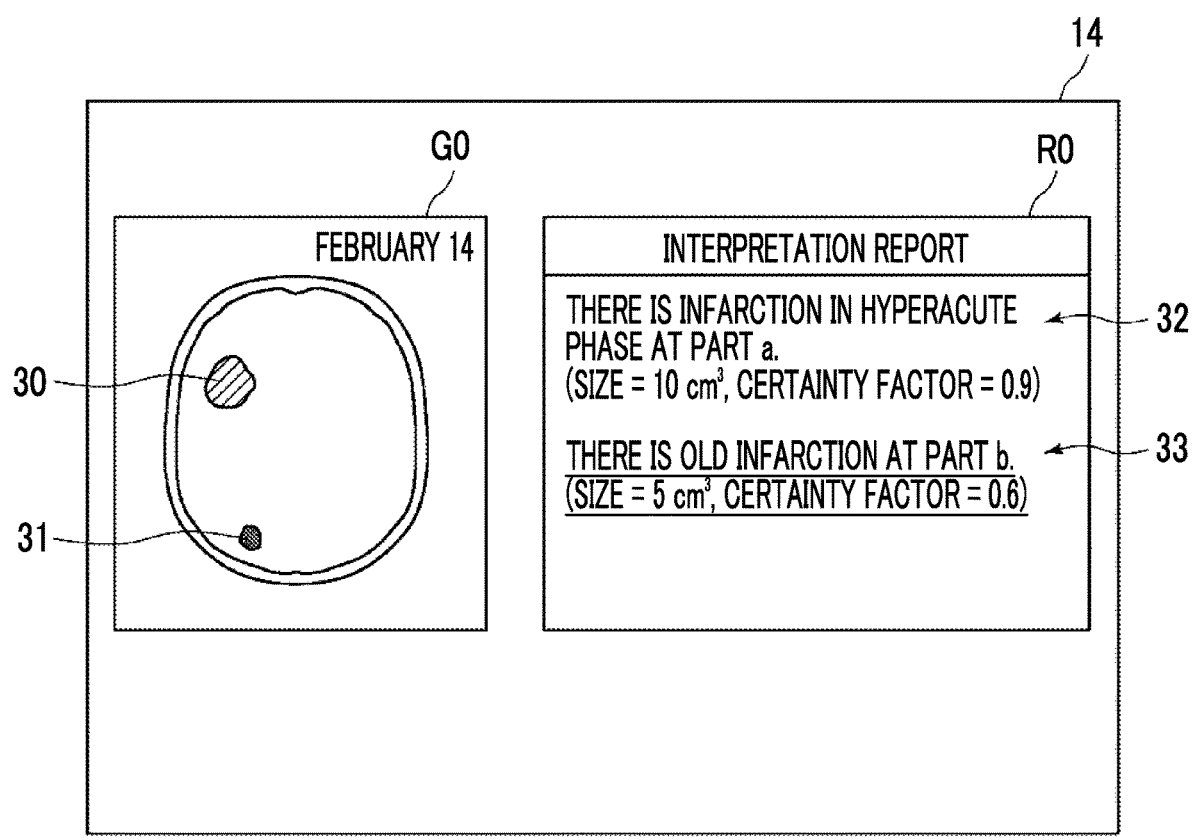
FIG. 3 is a diagram showing a medical image and an interpretation report displayed on a display in the first embodiment.

The display control unit 23 displays a medical image and an interpretation report on the display 14. FIG. 3 is a diagram showing a medical image and an interpretation report displayed on the display 14 in the first embodiment. As shown in FIG. 3, a medical image G0 and an interpretation report R0 are displayed on the display 14. In the medical image G0, infarction regions 30 and 31 extracted by the analysis unit 21 are highlighted. In FIG. 3, highlighting is given by hatching the region. In the medical image G0, the imaging date is superimposed and displayed. The interpretation report R0 includes a sentence 32 of "there is an infarction in the hyperacute phase at the part a, size=10 cm$^3$, certainty factor=0.9" and a sentence 33 of "there is an old infarction at the part b, size=5 cm$^3$, certainty factor=0.6", both of which include a description of the disease. In the sentence 33, an underline indicating that a link is set is given.

Figure 4:
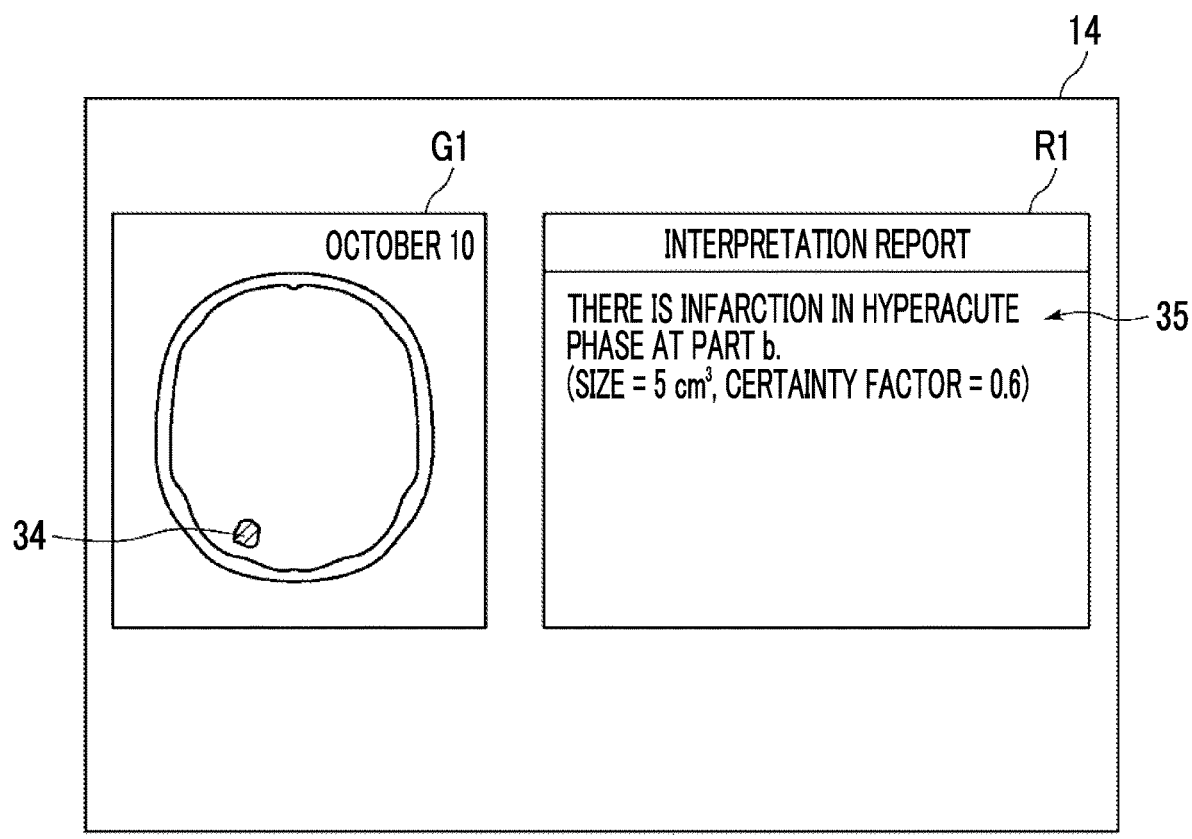
FIG. 4 is a diagram showing a past medical image and a past interpretation report displayed on the display in the first embodiment.

The operator gives an instruction for the sentence 33 in which a link is set using the input unit 15, so that a past interpretation report of the patient can be downloaded from the interpretation report database 8 and a past medical image associated with the past interpretation report can be downloaded from the image database 6 and the past interpretation report and the past medical image can be displayed on the display 14. FIG. 4 is a diagram showing a past medical image and a past interpretation report that are displayed on the display 14. As shown in FIG. 4, a past medical image G1 and a past interpretation report R1 are displayed on the display 14. In the past medical image G1, an infarction region 34 is highlighted at the part b. Since the infarction region 34 has the same infarction type as the infarction region 30 in FIG. 3, the infarction region 34 is hatched in the same manner as the infarction region 30. The past interpretation report R1 includes a sentence 35 of "there is an infarction in the hyperacute phase at the part b, size=5 cm$^3$, certainty factor=0.6", which includes a description of the disease.

In response to the operator's instruction to modify one of the disease region in the medical image G0 and the description of the disease in the interpretation report R0 using the input unit 15, the modification unit 24 modifies the other one of the disease region in the medical image G0 and the description of the disease in the interpretation report R0. That is, the modification unit 24 modifies the description of the disease in the interpretation report R0 in response to an instruction to modify the disease region in the medical image G0. In addition, the modification unit 24 modifies the disease region in the medical image G0 in response to an instruction to modify the description of the disease in the interpretation report R0.

Figure 5:
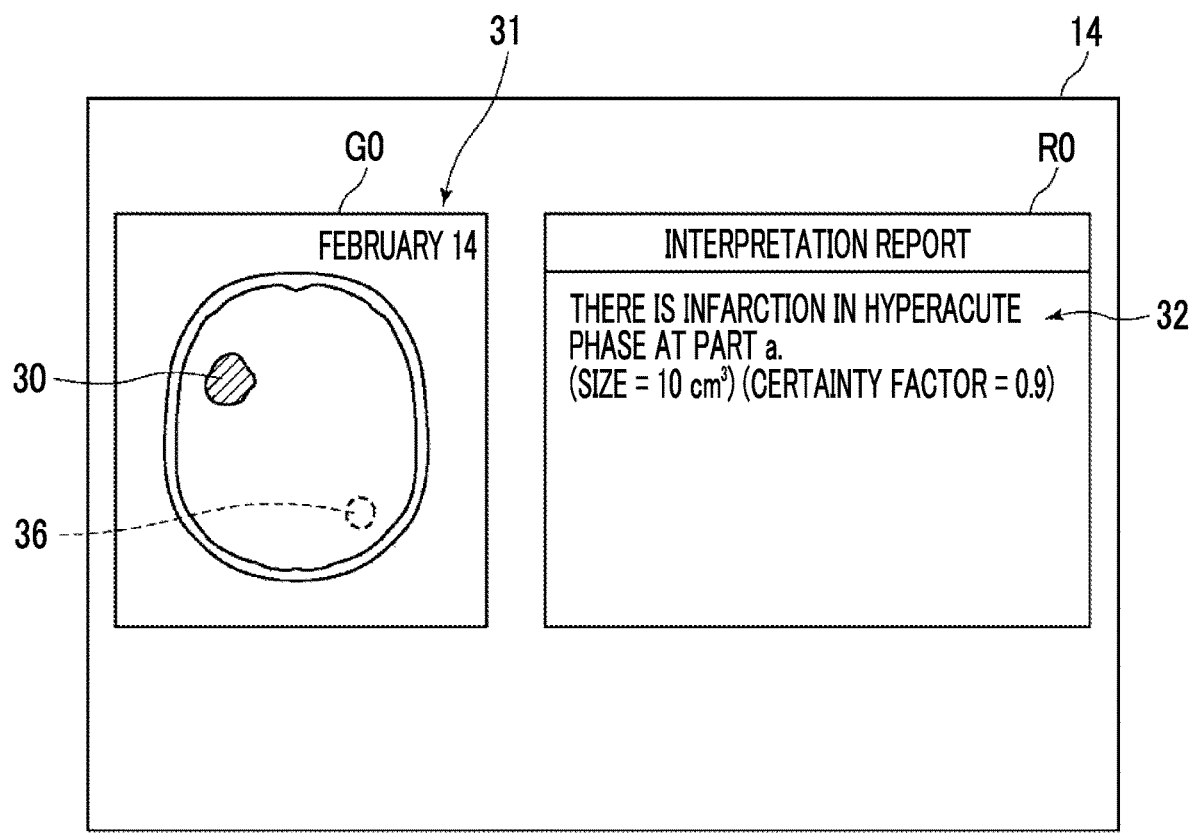
FIG. 5 is a diagram illustrating modification processing in the first embodiment.
Figure 6:
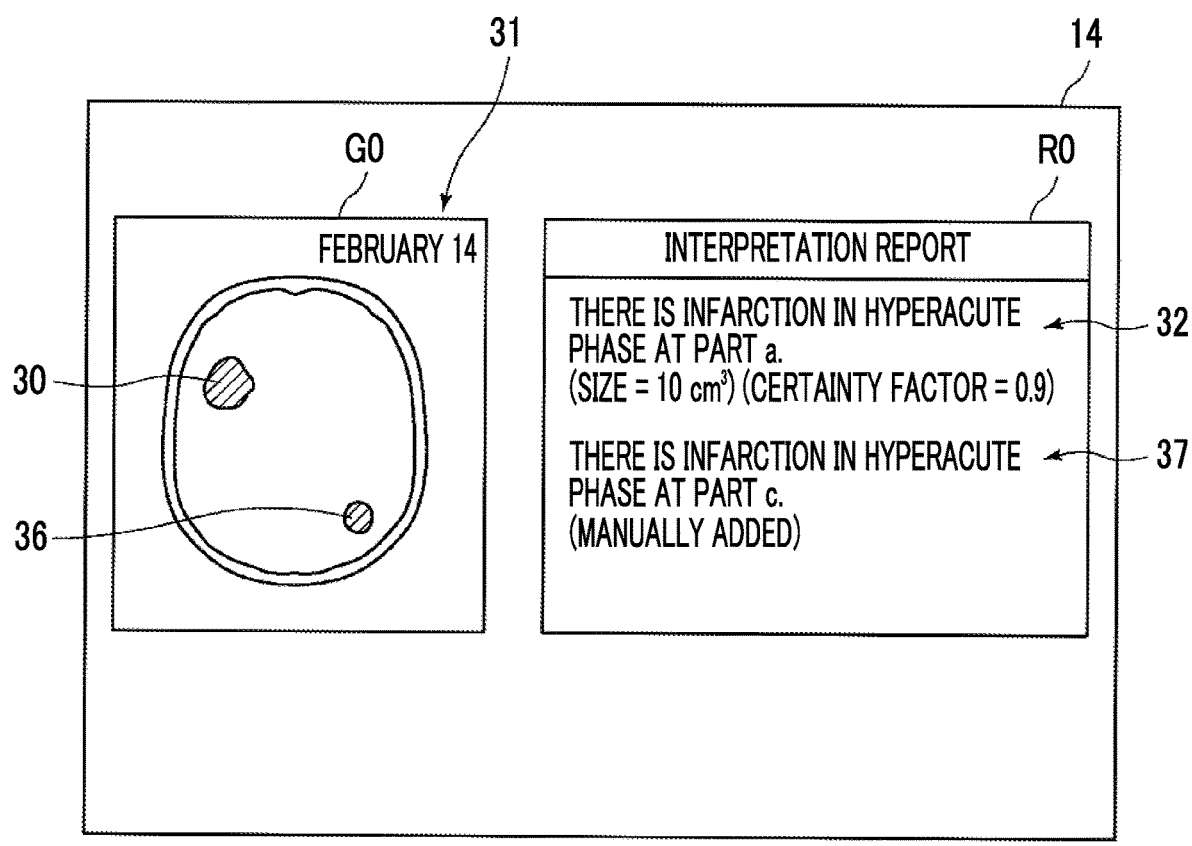
FIG. 6 is a diagram illustrating modification processing in the first embodiment.

FIGS. 5 and 6 are diagrams illustrating modification processing in the first embodiment. In FIG. 5, it is assumed that only the infarction region 30 is highlighted in the medical image G0 and the interpretation report R0 includes only the sentence 32. In addition, as shown in FIG. 5, it is assumed that a modification instruction to add an infarction region 36 to a part c as a disease region in the medical image G0 is made from the input unit 15. As a result, the modification unit 24 creates a sentence 37 of "there is an infarction in the hyperacute phase at the part c", and adds the sentence 37 to the interpretation report R0 as shown in FIG. 6. Here, in the sentence 37, characters "manually added" indicating that the sentence 37 was manually added are displayed. It is unknown whether the type of the infarction region is in the hyperacute phase or old only with an instruction to add the infarction region to the medical image G0. In the present embodiment, the modification unit 24 creates a sentence "there is an infarction in the hyperacute phase at the part c" using the characters "hyperacute phase" as the initial display. In a case where the infarction region 36 is old, the operator may modify "hyperacute phase" included in the sentence 37 to "old".

On the contrary, in a case where the operator makes a modification instruction to add the sentence 37 of "there is an infarction in the hyperacute phase at the part c" to the interpretation report R0, the modification unit 24 sets the infarction region 36 in the hyperacute phase at the part c of the medical image G0 and highlight the infarction region 36.

Figure 7:
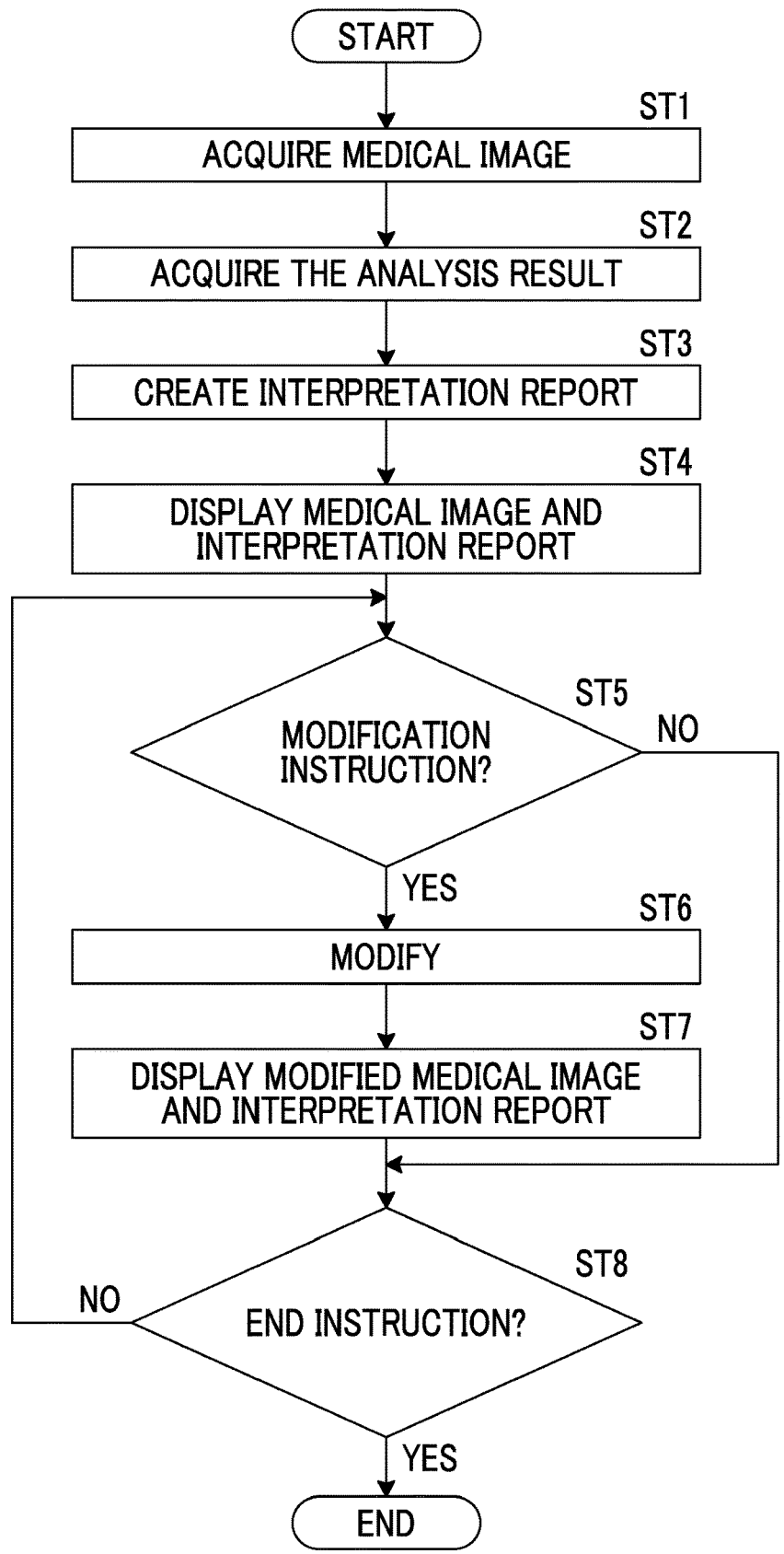
FIG. 7 is a flowchart showing the process performed in the first embodiment.

Next, the process performed in the first embodiment will be described. FIG. 7 is a flowchart showing the process performed in the present embodiment. The process starts in a case where the interpretation WS 3, that is, the medical image display device 10 receives a notification that a new medical image has been stored in the image server 5, the analysis unit 21 of the medical image display device 10 acquires the medical image G0 from the image server 5 (step ST1), and the analysis unit 21 analyzes the medical image G0 to acquire the analysis result (step ST2). Then, the interpretation report creation unit 22 creates the interpretation report R0 on the disease based on the analysis result (step ST3). Then, the display control unit 23 displays the medical image G0 and the interpretation report R0 on the display 14 (step ST4).

Then, the modification unit 24 determines whether or not there is an instruction to modify one of a disease region in the medical image G0 and a description of the disease in the interpretation report R0 (step ST5). In a case where step ST5 is negative, the process proceeds to step ST8. In a case where step ST5 is positive, the other one of the disease region in the medical image G0 and the description of the disease in the interpretation report R0 is modified in response to the modification instruction (step ST6). The display control unit 23 displays the modified medical image G1 or the modified interpretation report R1 (step ST7). Then, it is determined whether or not there is an end instruction (step ST8). In a case where step ST8 is negative, the process proceeds to step ST5. In a case where step ST8 is positive, the process is ended.

As described above, in the present embodiment, the medical image G0 including the disease region and the interpretation report R0 including the description of the disease are displayed on the display 14, and the other one of the disease region in the medical image G0 and the description of the disease in the interpretation report R0 is modified in response to the instruction to modify one of the disease region in the medical image G0 and the description of the disease in the interpretation report R0. For this reason, even in a case where it is necessary to modify both the medical image G0 and the interpretation report R0, the other one is modified according to the modification of one of the medical image G0 and the interpretation report R0. Therefore, it is possible to reduce the burden on the operator (radiologist) who modifies the medical image G0 and the interpretation report R0.

In the first embodiment described above, the interpretation report creation unit 22 creates a sentence including findings as the interpretation report R0. However, the invention is not limited thereto, and an interpretation report including ASPECTS may be created. Hereinafter, this will be described as a second embodiment. In the second embodiment, the configuration of a medical image display device is the same as the configuration of the medical image display device according to the first embodiment shown in FIG. 2, and only the processing is different. Accordingly, the detailed description of the device will be omitted herein. In the second embodiment, a medical image is a three-dimensional CT image, and the analysis unit 21 analyzes a tomographic image of a basal ganglia level and a tomographic image of a radiological crown level included in a three-dimensional CT image and performs the analysis so as to extract an infarction region.

Figure 8:
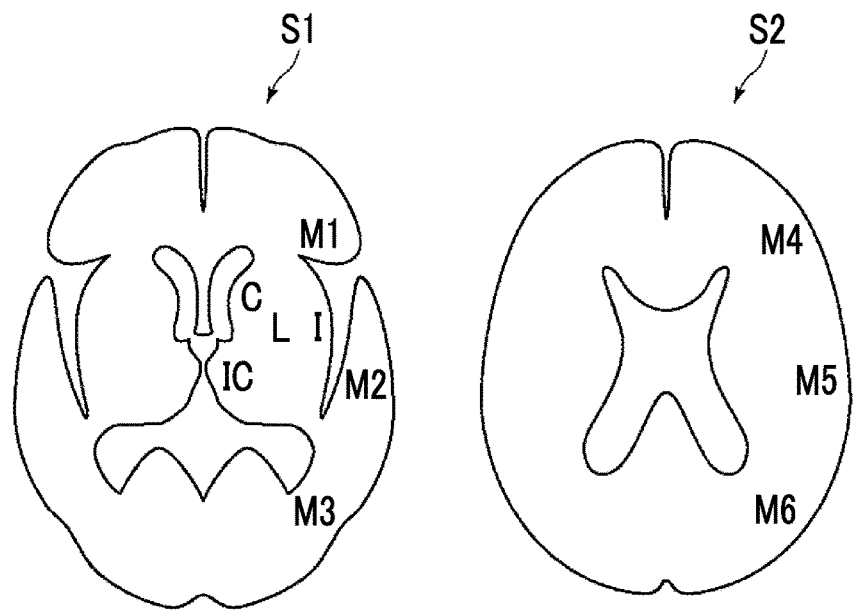
FIG. 8 is a schematic diagram of the brain illustrating ASPECTS.

FIG. 8 is a schematic diagram of the brain illustrating ASPECTS. ASPECTS is an abbreviation for Alberta Stroke Program Early CT Score, and is a scoring method for quantifying the early CT sign of simple CT for cerebral infarction in the middle cerebral artery region. Specifically, in a case where the medical image is a CT image, the ASPECTS is a method in which the middle cerebral artery region is classified into ten regions in two representative cross sections (basal ganglia level and radiological crown level), the presence or absence of early ischemic change is evaluated for each region, and the positive part is scored by the penalty point method. In the ASPECTS, left and right middle cerebral artery regions are classified into seven regions of C, I, L, IC, and M1 to M3 for a tomographic image 51 of the basal ganglia level of the brain, and left and right middle cerebral artery regions are classified into three regions of M4 to M6 for a tomographic image S2 of the radiological crown level. In FIG. 8, in order to simplify the description, the regions are shown only in the right brain. In the second embodiment, an infarction region is extracted from the medical image G0, the positions of the ten regions in the infarction region are specified, and the analysis result is generated.

In the second embodiment, the interpretation report creation unit 22 creates an interpretation report including ASPECTS.

Figure 9:
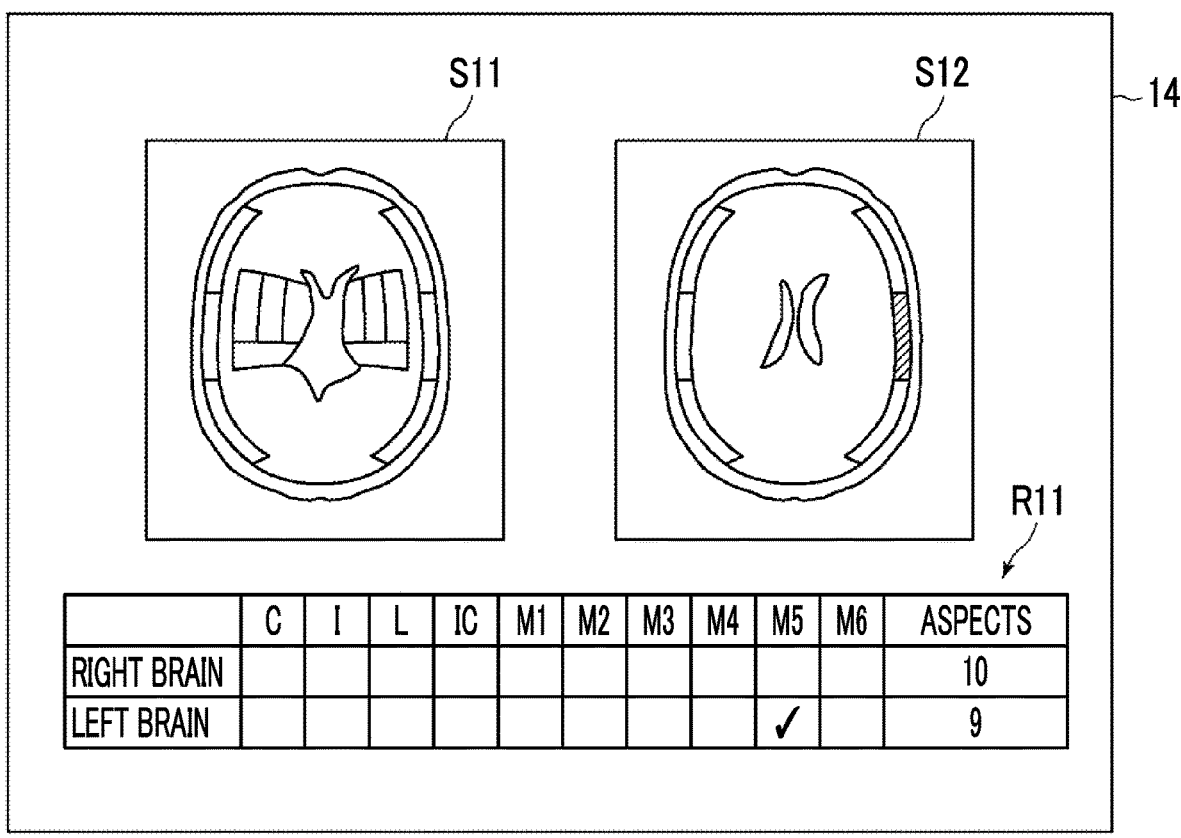
FIG. 9 is a diagram showing a medical image and an interpretation report displayed on a display in a second embodiment.

In the second embodiment, the display control unit 23 displays a medical image and an interpretation report including ASPECTS on the display 14. FIG. 9 is a diagram showing medical images and an interpretation report including ASPECTS, which are displayed on the display 14, in the second embodiment. As shown in FIG. 9, in the second embodiment, a tomographic image S11 of the basal ganglia level of the brain and a tomographic image S12 of the radiological crown level of the brain are displayed as medical images. The tomographic images S11 and S12 are images in which the brain is viewed from the foot side to the head side of the human body. Therefore, in the tomographic images S11 and S12 shown in FIG. 9, the right side is the left brain and the left side is the right brain. As shown in FIG. 9, ten regions of ASPECTS are shown in the tomographic image S11 and the tomographic image S12. A region including an infarction is highlighted. In FIG. 9, highlighting is given by hatching the region. An interpretation report R11 includes a check on whether or not each of ten regions of the left and right brains in ASPECTS includes an infarction region and ASPECTS. Here, in the second embodiment, since no infarction region is extracted in the right brain, neither region is highlighted in the tomographic images S11 and S12, and no check is made for any region of the interpretation report R11. Therefore, ASPECTS for the right brain is ten points. In the left brain, an infarction region is extracted in the region M5. Accordingly, the region M5 of the tomographic image S12 is highlighted, and a check is given to the region M5 of the left brain in the interpretation report R11. Therefore, ASPECTS for the left brain is nine points.

Ten regions of ASPECTS in the medical image G0 are specified by performing alignment between the medical image G0 and a standard brain image. The standard brain image is a three-dimensional brain image showing a brain having a standard shape and size and a standard density (pixel value), that is, a standard brain. The standard brain image can be generated by extracting brains from a plurality of brain images, which are acquired by imaging the heads of a plurality of healthy persons with a three-dimensional image capturing apparatus, and averaging the plurality of extracted brains. The standard brain image may be created by computer graphics or the like. Alternatively, a brain image of one healthy person may be used as a standard brain image.

Here, the standard brain image is divided into ten regions of ASPECTS. In the second embodiment, the display control unit 23 performs alignment between the medical image G0 and the standard brain image, specifies ten regions of the ASPECTS in the medical image G0, and divides and displays the ten regions of the ASPECTS as shown in FIG. 9 in the tomographic images S11 and S12 to be displayed.

Figure 10:
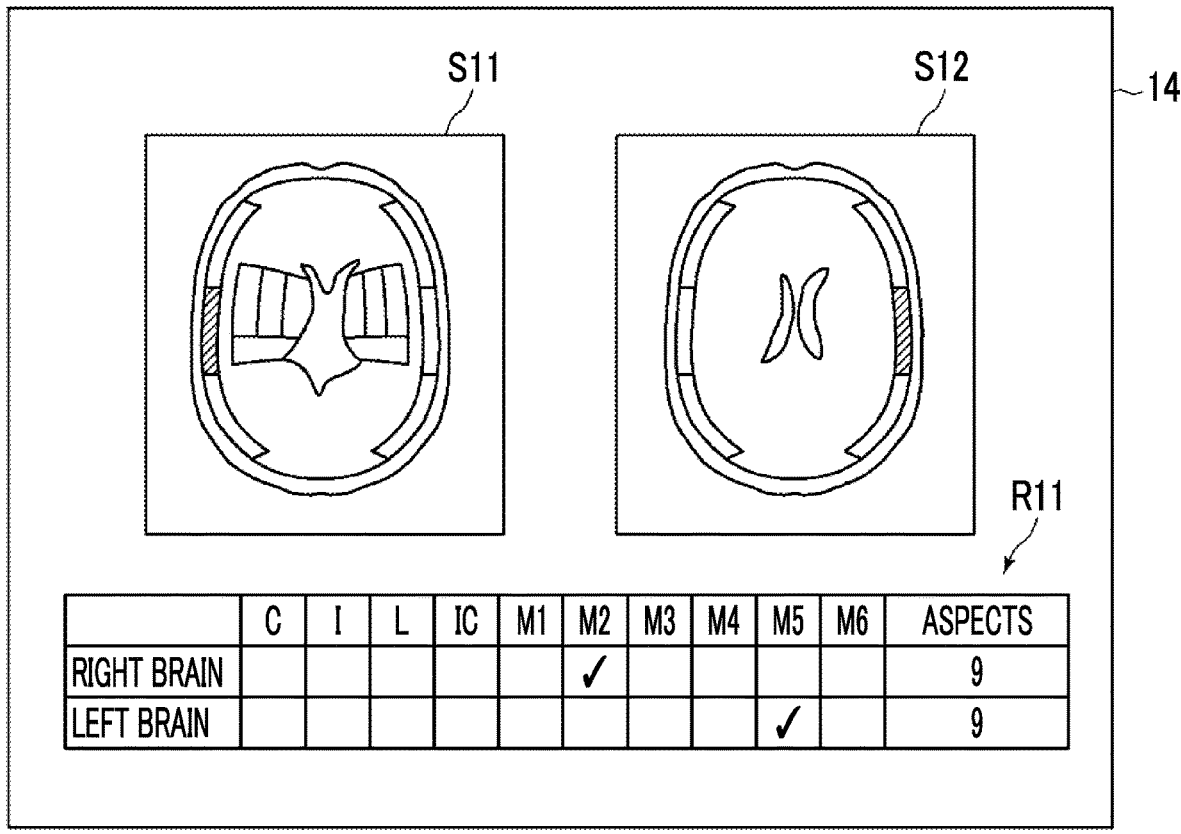
FIG. 10 is a diagram showing a medical image and an interpretation report displayed on the display in the second embodiment.

On the other hand, also in the second embodiment, the modification unit 24 modifies the other one of the disease region in the medical image G0 and the description of the disease region in the interpretation report R0 in response to the instruction to modify one of the disease region in the medical image G0 and the description of the disease region in the interpretation report R0. That is, in the second embodiment, in a case where the operator modifies the interpretation report R11, the tomographic images S11 and S12 are modified. For example, as shown in FIG. 10, in a case where a check is given to the region M2 of the right brain in the interpretation report R11, the modification unit 24 highlights the region M2 of the right brain in the tomographic image S11. On the other hand, in a case where an instruction to highlight the region M2 of the right brain in the tomographic image S11 is made, the modification unit 24 gives a check to the region M2 of the right brain in the interpretation report R11. In any case, the ASPECTS of the right brain is nine points.

Figure 11:
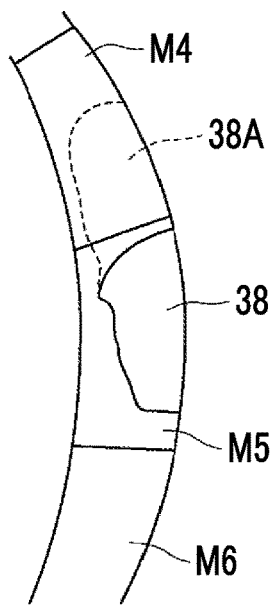
FIG. 11 is a diagram illustrating the modification of an infarction region in the second embodiment.
Figure 12:
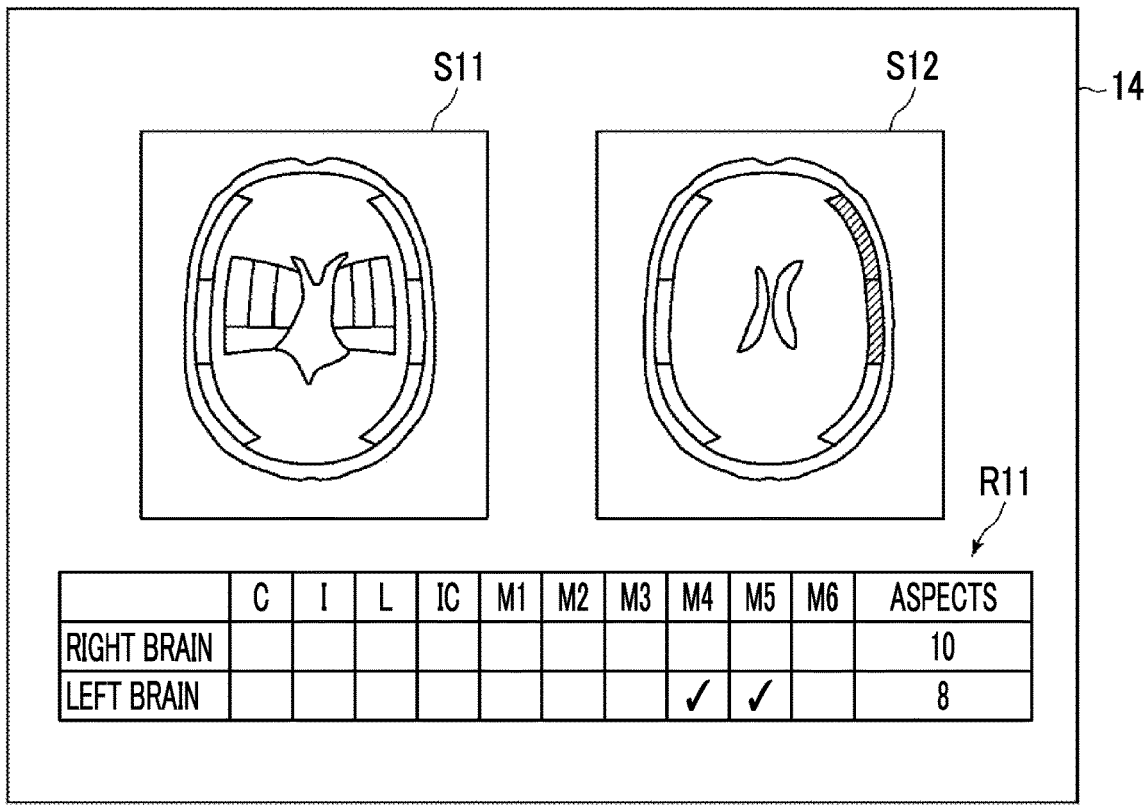
FIG. 12 is a diagram showing a medical image and an interpretation report displayed on the display in the second embodiment.

In the tomographic images S11 and S12, the operator can also modify an infarction region using the input unit 15. FIG. 11 is a diagram illustrating modification of an infarction region in the second embodiment. FIG. 11 shows a part of the region of the left brain of the tomographic image S12 in an enlarged manner. As shown in FIG. 11, in a case where an infarction region 38 is extracted by the analysis processing of the analysis unit 21, the region M5 of the left brain is highlighted in the tomographic image S12 and the region M5 of the left brain is checked in the interpretation report R11 in the same manner as in FIG. 9. However, in a case where the radiologist interprets the tomographic image S12, it is assumed that an infarction region 38A extending over the regions M4 and M5 can be checked as shown by the broken line in FIG. 11. In this case, the radiologist modifies the infarction region 38 to the infarction region 38A in the tomographic image S12. According to this instruction, as shown in FIG. 12, the modification unit 24 highlights the regions M4 and M5 of the left brain in the tomographic image S12, and further gives a check to the region M4 of the left brain in the interpretation report R11. As a result, the ASPECTS of the left brain is eight points.

In the second embodiment described above, the interpretation report R11 includes ASPECTS. However, in addition to the ASPECTS, the same sentence as in the first embodiment may be included. For example, a sentence, such as "there is an infarction region in the hyperacute phase in the region M5" may be included.

In the embodiment described above, the medical image display device 10 in the interpretation WS 3 comprises the analysis unit 21 and the interpretation report creation unit 22. However, an external analysis server, an interpretation report creation server, or the like may analyze a medical image and create an interpretation report based on the analysis result.

Figure 13:
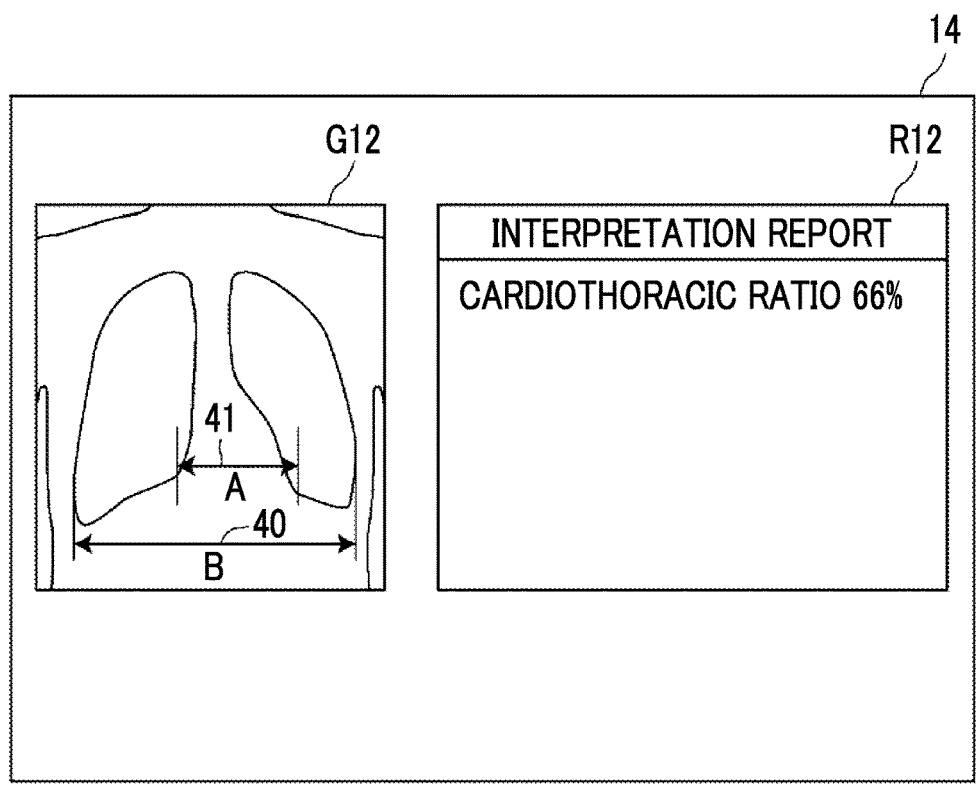
FIG. 13 is a diagram showing a medical image of the heart and an interpretation report displayed on the display.

In the embodiment described above, the CT image and the MRI image of the brain are used as medical images. However, medical images of other parts may be used. For example, a medical image of the heart including a disease of cardiac enlargement may be analyzed, the region of the heart may be extracted as a disease region, and an interpretation report may include a cardiothoracic ratio. FIG. 13 is a diagram showing a medical image and an interpretation report of the heart displayed on the display 14. As shown in FIG. 13, a medical image G12, which is a simple X-ray image of the heart, and an interpretation report R12 are displayed on the display 14. In the medical image G12, an arrow 40 indicating a range A of the chest and an arrow 41 indicating a range B of the heart are displayed. The interpretation report R12 includes a cardiothoracic ratio (B/A× 100%).

The radiologist that is an operator can modify the ranges indicated by the arrows 40 and 41 in the medical image G12. In addition, in the interpretation report R12, the value of the cardiothoracic ratio can be modified. In a case where the ranges indicated by the arrows 40 and 41 in the medical image G12 are modified, the modification unit 24 calculates the cardiothoracic ratio again to modify the interpretation report R12. In a case where the cardiothoracic ratio is modified in the interpretation report R12, the modification unit 24 may modify the ranges indicated by the arrows 40 and 41 in the medical image G12. In this case, only one of the arrows 40 and 41 may be modified.

What is claimed is:

1. A medical image display device, comprising at least processor, wherein the processor is configured to:
   access an interpretation report that is generated by analyzing a medical image, including a plurality of voxels, using machine learning, and determine that the medical image includes a region of a disease when at least one of the plurality of voxels is equal to or greater than a predetermined threshold value;
   display the medical image including the disease and the interpretation report including a description of the disease on a display;
   determine whether there is an instruction to modify the description of the disease in the interpretation report that was generated;
   determine that there is the instruction to modify the description of the disease in the interpretation report that was generated; and
   modify, in response to determining that there is the instruction to modify the description of the disease in the interpretation report that was generated, the region of the disease in the medical image.

2. The medical image display device according to claim 1, wherein the interpretation report includes a certainty factor that the region of the disease in the medical image is a disease.

3. The medical image display device according to claim 1, wherein the medical image is a brain image, and the disease is cerebral infarction.

4. The medical image display device according to claim 1, wherein the interpretation report is associated with a past interpretation report of the same patient.

5. The medical image display device according to claim 4, wherein the interpretation report is associated with a past medical image of the same patient associated with the past interpretation report.

6. The medical image display device according to claim 1, wherein the interpretation report includes ASPECTS.

7. The medical image display device according to claim 1, further comprising:
   an analysis unit that analyzes the medical image and acquires an analysis result on the disease.

8. The medical image display device according to claim 7, further comprising:
   an interpretation report creation unit that creates the interpretation report based on the analysis result.

9. A medical image display method, comprising:
   accessing an interpretation report that is generated by analyzing a medical image, including a plurality of voxels, using machine learning, and determine that the medical image includes a region of a disease when at least one of the plurality of voxels is equal to or greater than a predetermined threshold value;
   displaying, via at least one processor, the medical image including the disease and the interpretation report including a description of the disease on a display;
   determining whether there is an instruction to modify the description of the disease in the interpretation report that was generated;
   determining that there is the instruction to modify the description of the disease in the interpretation report that was generated; and
   modifying, via the at least one processor, in response to determining that there is the instruction to modify the description of the disease in the interpretation report that was generated, the region of the disease in the medical image.

10. A non-transitory computer-readable storage medium that stores a medical image display program, executable by at least one processor, causing a computer to execute:
    access an interpretation report that is generated by analyzing a medical image, including a plurality of voxels, using machine learning, and determine that the medical image includes a region of a disease when at least one of the plurality of voxels is equal to or greater than a predetermined threshold value;
    display the medical image including the disease and the interpretation report including a description of the disease on a display;
    determine whether there is an instruction to modify the description of the disease in the interpretation report that was generated;
    determine that there is the instruction to modify the description of the disease in the interpretation report that was generated; and
    modify, in response to determining that there is the instruction to modify the description of the disease in the interpretation report that was generated, the region of the disease in the medical image.

11. A medical image display device, comprising at least one processor, wherein the processor is configured to:
analyze, using machine learning, a medical image including a disease, the medical image including a plurality of voxels, and determine that the medical image includes a region of a disease when at least one of the plurality of voxels is equal to or greater than a predetermined threshold value;
create an interpretation report including a description of the disease based on the analysis result;
display the medical image in which the region of the disease is specified and the interpretation report on a display;
determine whether there is an instruction to modify the description of the disease in the interpretation report that was generated;
determine that there is the instruction to modify the description of the disease in the interpretation report that was generated; and
modify, in response to determining that there is the instruction to modify one of a region of the disease in the medical image and the description of the disease in the interpretation report that was generated, the other one of the region of the disease in the medical image and the description of the disease in the interpretation report.

12. A medical image display method, comprising:
analyzing, via at least one processor, using machine learning, a medical image including a disease, the medical image including a plurality of voxels, and determining an analysis result that the medical image includes a region of the disease when at least one of the plurality of voxels is equal to or greater than a predetermined threshold value;
creating, via the at least one processor, an interpretation report including a description of the disease based on the analysis result;
displaying, via the at least one processor, the medical image in which the region of the disease is specified and the interpretation report on a display;
determining whether there is an instruction to modify the description of the disease in the interpretation report that was generated:
determining that there is the instruction to modify the description of the disease in the interpretation report that was generated; and
modifying, via the at least one processor, in response to determining that there is the instruction to modify one of a region of the disease in the medical image and the description of the disease in the interpretation report that was generated, the other one of the region of the disease in the medical image and the description of the disease in the interpretation report.

13. A non-transitory computer-readable storage medium that stores a medical image display program, executable by at least one processor, causing a computer to execute:
analyze, using machine learning, a medical image including a disease, the medical image including a plurality of voxels, and determine an analysis result that the medical image includes a region of the disease when at least one of the plurality of voxels is equal to or greater than a predetermined threshold value;
create an interpretation report including a description of the disease based on the analysis result;
display the medical image in which the region of the disease is specified and the interpretation report on a display;
determine whether there is an instruction to modify the description of the disease in the interpretation report that was generated;
determine that there is the instruction to modify the description of the disease in the interpretation report that was generated; and
modify, in response to determining that there is the instruction to modify, one of a region of the disease in the medical image and the description of the disease in the interpretation report that was generated, the other one of the region of the disease in the medical image and the description of the disease in the interpretation report.

* * * * *